United States Patent
Spahn et al.

(10) Patent No.: US 11,779,493 B2
(45) Date of Patent: Oct. 10, 2023

(54) THERAPEUTIC CUSHIONING BOOT

(71) Applicant: EHOB, Inc., Indianapolis, IN (US)

(72) Inventors: James G. Spahn, Carmel, IN (US);
Aaron D. Kadel, Indianapolis, IN (US);
James Q. Bui, Carmel, IN (US);
Sharon Lucich, Indianapolis, IN (US)

(73) Assignee: EHOB, Inc., Indianapolis, IN (US)

( * ) Notice: Subject to any disclaimer, the term of this patent is extended or adjusted under 35 U.S.C. 154(b) by 328 days.

(21) Appl. No.: 17/064,037

(22) Filed: Oct. 6, 2020

(65) Prior Publication Data

US 2021/0015681 A1      Jan. 21, 2021

Related U.S. Application Data

(63) Continuation of application No. 14/837,686, filed on Aug. 27, 2015, now Pat. No. 10,806,633.
(60) Provisional application No. 62/042,757, filed on Aug. 27, 2014.

(51) Int. Cl.
| | |
|---|---|
| *A61F 13/00* | (2006.01) |
| *A61F 5/00* | (2006.01) |
| *A61F 13/06* | (2006.01) |
| *A61F 5/01* | (2006.01) |
| *A61F 5/30* | (2006.01) |

(52) U.S. Cl.
CPC .......... *A61F 13/069* (2013.01); *A61F 5/0111* (2013.01); *A61F 5/30* (2013.01); *A61F 13/00017* (2013.01); *A61F 13/064* (2013.01)

(58) Field of Classification Search
None
See application file for complete search history.

(56) References Cited

U.S. PATENT DOCUMENTS

| | | | |
|---|---|---|---|
| 1,970,081 | A | 8/1934 | Eisendrath |
| 2,088,511 | A | 7/1937 | Frei |
| 2,613,455 | A | 10/1952 | Amico |
| 2,794,270 | A | 6/1957 | Dubner |
| 2,906,261 | A | 9/1959 | Craig |
| 2,911,657 | A | 11/1959 | Streeter |
| 3,021,846 | A | 2/1962 | Scholl |
| 3,237,319 | A | 3/1966 | Hanson |
| 3,462,763 | A | 8/1969 | Schneider |
| 3,511,233 | A | 5/1970 | Holy, Jr. |

(Continued)

FOREIGN PATENT DOCUMENTS

GB      496056      11/1938

OTHER PUBLICATIONS

Spahn, James, The Science of Pressure Ulcer Development, Prevention and Treatment with a View of New Approaches to Predict and Model, White Paper, www.EHOB.com, available before Dec. 31, 2012.

*Primary Examiner* — Kim M Lewis
(74) *Attorney, Agent, or Firm* — Maginot, Moore & Beck, LLP

(57) ABSTRACT

A therapeutic cushioning boot includes a foot portion configured to receive a foot of a user, and a leg portion configured to receive a leg of the user. The leg portion includes at least a first support chamber and a second support chamber. A first fiberfill material is provided in the first support chamber at a first concentration, and a second fiberfill material provided in the second support chamber at a second concentration that is less than the first concentration.

18 Claims, 13 Drawing Sheets

(56) References Cited

U.S. PATENT DOCUMENTS

| | | |
|---|---|---|
| 3,527,209 A | 9/1970 | Baker |
| 3,529,369 A | 9/1970 | Drago |
| 3,552,044 A | 1/1971 | Wiele |
| 3,606,884 A | 9/1971 | Peter |
| 3,641,688 A | 2/1972 | Von Den Berken |
| 3,693,270 A | 9/1972 | Murray |
| 3,707,784 A | 1/1973 | Stafford |
| 3,750,310 A | 8/1973 | Messner et al. |
| 3,785,070 A | 1/1974 | Stafford |
| 3,814,088 A | 6/1974 | Raymond |
| 3,827,430 A | 8/1974 | Fadden |
| 3,950,864 A | 4/1976 | Cooper et al. |
| 4,076,022 A | 2/1978 | Walker |
| 4,182,055 A | 1/1980 | Turner et al. |
| 4,197,845 A | 4/1980 | Berguer |
| 4,401,113 A | 8/1983 | Incorvaia |
| 4,454,871 A | 6/1984 | Mann et al. |
| 4,472,890 A | 9/1984 | Gilbert |
| 4,478,214 A | 10/1984 | Lamont |
| 4,520,803 A | 6/1985 | Quest |
| 4,566,197 A | 1/1986 | Sitzes |
| 4,572,169 A | 2/1986 | Mauldin et al. |
| 4,603,493 A | 8/1986 | Eston |
| 4,627,179 A | 12/1986 | McElroy |
| 4,628,621 A | 12/1986 | Brown |
| 4,642,912 A | 2/1987 | Wildman et al. |
| 4,669,142 A | 6/1987 | Meyer |
| 4,706,316 A | 11/1987 | Tanzi |
| 4,747,410 A | 5/1988 | Cohen |
| 4,782,605 A | 11/1988 | Chapnick |
| 4,813,162 A | 3/1989 | Harris |
| 4,832,010 A | 5/1989 | Lerman |
| 4,841,648 A | 6/1989 | Shaffer et al. |
| 4,841,957 A | 6/1989 | Wooten et al. |
| 4,974,583 A | 12/1990 | Freitas |
| 5,003,708 A | 4/1991 | Daley |
| 5,007,416 A | 4/1991 | Burns et al. |
| 5,020,523 A | 6/1991 | Bodine |
| 5,036,838 A | 8/1991 | Sherman |
| 5,050,598 A | 9/1991 | Tucker |
| 5,050,620 A | 9/1991 | Cooper |
| 5,088,479 A | 2/1992 | Detoro |
| 5,092,347 A | 3/1992 | Shaffer et al. |
| 5,123,180 A | 6/1992 | Nannig et al. |
| 5,143,058 A | 9/1992 | Luber et al. |
| 5,154,695 A | 10/1992 | Farris et al. |
| 5,162,041 A | 11/1992 | Simmons |
| 5,176,624 A | 1/1993 | Kuehnreich |
| 5,184,409 A | 2/1993 | Brown |
| 5,216,825 A | 6/1993 | Brum |
| 5,224,925 A | 7/1993 | Vam |
| 5,226,245 A | 7/1993 | Lamont |
| 5,230,333 A | 7/1993 | Yates et al. |
| 5,256,135 A | 10/1993 | Avihod |
| 5,329,705 A | 7/1994 | Grim et al. |
| 5,341,624 A | 8/1994 | Kaye |
| 5,367,789 A | 11/1994 | Lamont |
| 5,368,551 A | 11/1994 | Zuckerman |
| 5,370,133 A | 12/1994 | Darby et al. |
| 5,372,576 A | 12/1994 | Hicks |
| 5,393,303 A | 2/1995 | Shiono |
| 5,403,265 A | 4/1995 | Berguer et al. |
| 5,425,701 A | 6/1995 | Oster et al. |
| 5,429,588 A | 7/1995 | Young et al. |
| 5,437,621 A | 8/1995 | Andrews et al. |
| 5,449,339 A * | 9/1995 | Drennan .............. A61F 5/0195 128/882 |
| 5,456,659 A | 10/1995 | Gildersleeve et al. |
| 5,460,600 A | 10/1995 | Bieling |
| 5,496,358 A | 3/1996 | Rosenwald |
| 5,555,584 A | 9/1996 | Moore, III et al. |
| 5,569,173 A | 10/1996 | Vam |
| 5,569,174 A | 10/1996 | Vam |
| 5,591,221 A | 1/1997 | Owens |
| 5,609,570 A | 3/1997 | Lamont |
| 5,762,622 A | 6/1998 | Lamont |
| 5,797,862 A | 8/1998 | Lamont |
| 5,800,492 A | 9/1998 | Manker |
| 5,876,364 A * | 3/1999 | Herbst ................ A61F 13/069 602/27 |
| 5,913,841 A | 6/1999 | Lamont |
| 5,961,477 A | 10/1999 | Turtzo |
| 5,997,491 A | 12/1999 | Harris |
| 6,083,185 A | 7/2000 | Lamont |
| 6,260,221 B1 | 7/2001 | Grabell |
| 6,491,654 B2 | 12/2002 | Lamont |
| 6,866,043 B1 | 3/2005 | Davis |
| 2008/0178390 A1* | 7/2008 | DuDonis .............. A47C 20/021 5/655.5 |
| 2011/0180074 A1* | 7/2011 | Gainey ................ A61F 13/069 128/845 |
| 2012/0253250 A1 | 10/2012 | Spahn |
| 2016/0058642 A1* | 3/2016 | Drey .................... A61F 5/0111 128/845 |

* cited by examiner

THERAPEUTIC CUSHIONING BOOT

CROSS REFERENCE TO RELATED APPLICATIONS

This document is a continuation of U.S. patent application Ser. No. 14/837,686, filed Aug. 27, 2015, entitled "Fiber Filled Therapeutic Cushioning Boot," which claims priority to U.S. provisional patent application Ser. No. 62/042,757, filed Aug. 27, 2014, the entire contents of which are incorporated herein by reference.

BACKGROUND

1. Field of the Invention

Embodiments of the present invention generally relate to therapeutic cushioning boots. More particularly, embodiments of the present invention relate to a therapeutic cushioning boot for addressing various types of wounds, including, for example, pressure ulcers.

2. Description of the Related Art

As the occurrence of patient suffering from pressure ulcers continues to rise, there is an ongoing search among caregivers for improved ways of prevention and treatment, with a goal of identifying the most effective practices for addressing pressure ulcer care. For example, annually, approximately 2.5 million patients are treated in acute-care facilities for pressure ulcers. Further, patients with pressure ulcers are often three times more likely to be discharged to a long-term care facility than those who do not have pressure ulcers. Additionally, pressure ulcers are more likely to occur among those over age 65. Thus, since the U.S. population aged 65 and older is expected to double within the next 25 years, pressure ulcer risk and subsequent prevalence is expected to increase. Further, the older a person becomes, the more frail he/she may become. Because frailty and pressure ulcers share important risk factors such as incontinence, falls, delirium and functional decline, this will add to the growing concern of pressure ulcer risk in the aging baby boomer population. If proactive assessments, prevention and early intervention are not implemented for the growing, high risk geriatric population, it could pose a serious threat to the quality of health care delivered and already worrisome financial burdens. For example, the average cost associated with Stage IV treatment has been reported as $129,248.

Since pressure ulcer prevention, early intervention, treatment and care has become a quality indicator used by federal/state agencies for regulatory oversight and litigation proceedings, avoidance of the pressure ulcer problem must occur at all levels of care delivery and by all caregivers. For example. Table 1 below provides an indication of costs related to pressure ulcers.

TABLE 1

| COSTS RELATED TO PRESSURE ULCERS |
| --- |
| Federal/Financial Fines for Noncompliance $3,050 to $10,000 per day for development of an avoidable Stage IV Pressure Ulcer. |
| Legal Issue Related to Pressure Ulcers Long-term care legal cases per year increased from an average of 7 (1984 to Aug. 31, 1999) to 18 (Sep. 1, 1999). |

TABLE 1-continued

| COSTS RELATED TO PRESSURE ULCERS |
| --- |
| Recovery costs increased 40.3% from $3,359,259 in 1999 to $13,554,168 in 2002. Trend of plaintiffs winning verdicts is increasing which suggests facilities are being held to a higher standard of care. |

When the deep tissue injury component is considered in pressure ulcer staging, heel pressure ulcers are now first in occurrence. Further, typically support surfaces do not protect the ankle/foot/heel from pressure ulcers at all times. This is because recumbent physiological changes, hemodynamics (decreased circulatory perfusion and venous congestion), and the anatomy (multiple bony prominences with minimal subcutaneous tissue attached to the legs which acts as a fulcrum) of the region create a unique and challenging need that frequently exceeds the capabilities of a support surface to protect the ankle/foot/heel from mechanical stress injury. Support structures, particularly those addressing the ankle, foot, and heel, need to at least attempt to satisfy certain criteria, as indicated, for example, below in Table 2.

TABLE 2

| ANKLE/FOOT/HEEL PRODUCTS SHOULD: |
| --- |
| Elevate heel (off of surface) |
| Protect sides of foot and ankle |
| Neutralize weight of lower extremity (Delever) |
| Maintain and promote circulation |
| Address foot drop and lateral rotation of ankle |
| Allow access to the foot for inspection/treatment |
| Facilitate the musculoskeletal pump |
| Minimize risk for product contamination of surface or media |
| Be easy to clean |
| Fulfill regulatory requirements |
| Flame retardant |
| Bio-compatibility |
| Antimicrobial |
| FDA regulations |
| Good manufacturing process (ISO) |
| Address safety and comfort of patient |
| Lightweight |
| Pliable but durable |
| Latex free |

SUMMARY

In at least one exemplary embodiment, a therapeutic cushioning boot is provided that is configured to receive a human leg. The therapeutic cushioning boot comprises a rear panel, a first sidewall panel, and a second sidewall panel. The rear panel is configured to support a rear portion of the human leg and includes a first side, a second side, and a plurality of support chambers with a fill material positioned within each of the plurality of support chambers. The plurality of support chambers include a first support chamber proximate the first side of the rear panel, a second support chamber proximate the second side of the rear panel, and a third support chamber provided on the rear panel between the first support chamber and the second support chamber. The first sidewall panel is connected to the first side of the rear panel and is configured to engage a first side portion of the human leg. The second sidewall panel is connected to the second side of the rear panel and is configured to engage a second side portion of the human leg. The fill material in the first support chamber and the second support chamber is provided in greater concentration than the fill material in the third support chamber.

In at least one additional exemplary embodiment, a therapeutic cushioning boot includes a foot portion configured to receive a foot of a user and a leg portion configured to receive a leg of the user. The leg portion is connected to the foot portion and includes a plurality of support chambers arranged on a rear of the leg portion with a fill material positioned within each of the plurality of support chambers. The plurality of support chambers include a first support chamber proximate a first side of the leg portion, a second support chamber proximate a second side of the leg panel, and a third support chamber provided between the first support chamber and the second support chamber. The fill material in the first support chamber is a same material as the fill material in the second support chamber, and the fill material in the second support chamber is provided in greater concentration than the fill material in the third support chamber.

In yet another exemplary embodiment, a therapeutic cushioning boot includes a foot portion configured to receive a foot of a user, and a leg portion configured to receive a leg of the user. The leg portion includes at least a first support chamber and a second support chamber. A first fiberfill material is provided in the first support chamber at a first concentration, and a second fiberfill material provided in the second support chamber at a second concentration that is less than the first concentration.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings

Corresponding reference characters indicate corresponding parts throughout the several views. The exemplary embodiments set forth herein are not to be construed as limiting the scope of the invention in any manner.

DETAILED DESCRIPTION OF THE EMBODIMENTS

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all of the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
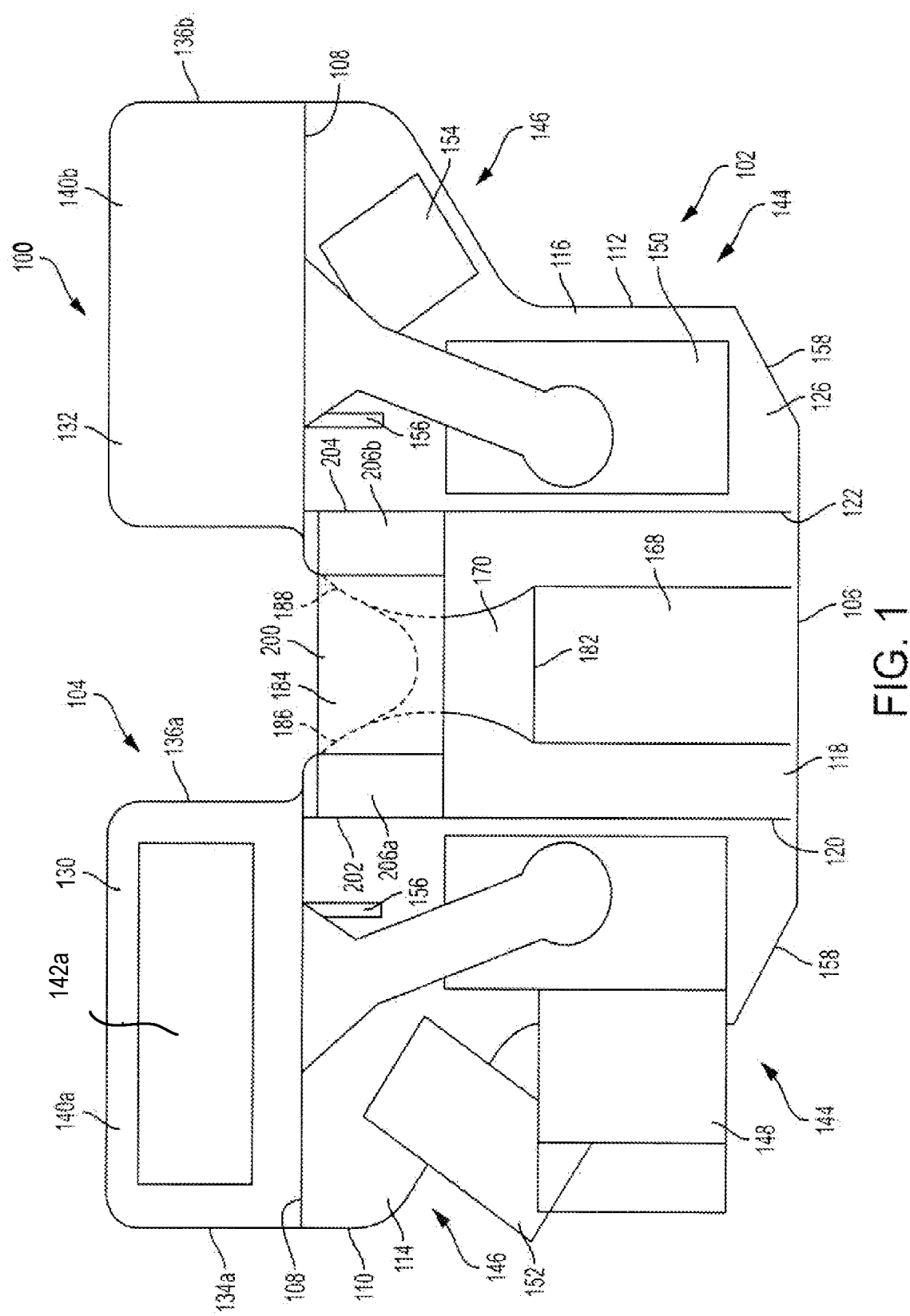
FIG. 1 illustrates an outside view of a therapeutic cushioning boot in an open and flattened condition according to an illustrated embodiment of the present invention.
Figure 2:
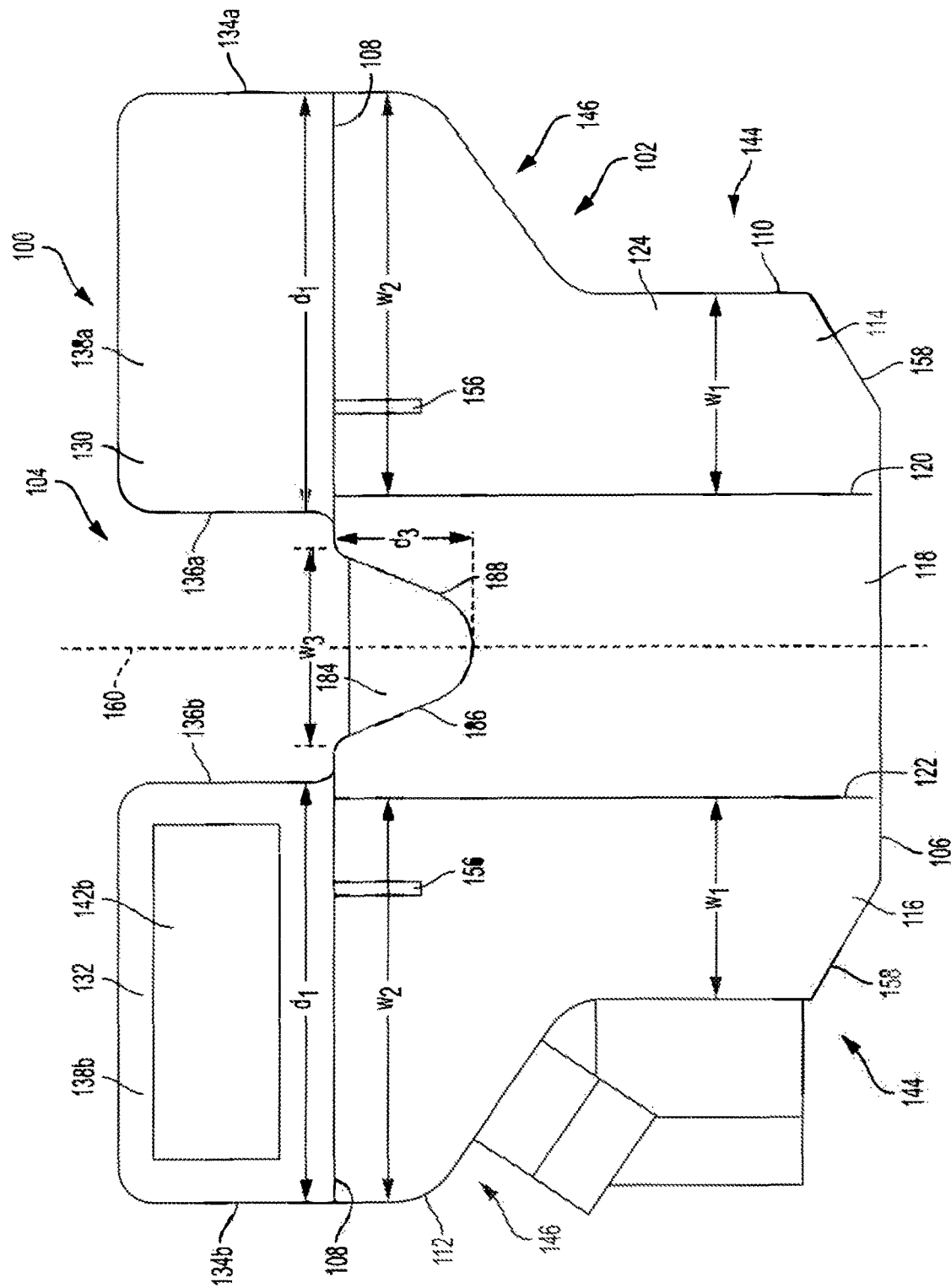
FIG. 2 illustrates an inside view of the therapeutic cushioning boot shown in FIG. 1.

FIGS. 1 and 2 illustrate outside and inside views, respectively, of a therapeutic cushioning boot 100 in an open and flattened condition, such as, for example, before the therapeutic cushioning boot 100 has been operably positioned about at least a portion of a lower leg region and/or foot of the user. In the illustrated embodiment, the therapeutic cushioning boot 100 may include a body portion 102 and a foot gate 104. The body portion 102 may include an upper edge 106, a lower edge 108, a first outer edge 110, and a second outer edge 112. Additionally, according to the illustrated embodiment, the body portion 102 may include a first sidewall panel 114, a second sidewall panel 116, and a rear panel 118. The first sidewall panel 114 may extend from the first outer edge 110 to a first inner boundary 120, while the second sidewall panel 116 may extend from the second outer edge 112 to a second inner boundary 122. The rear panel 118 may extend between the first and second inner boundaries 120, 122. According to certain embodiments, as discussed below, the first and second inner boundaries 120, 122 may provide pivot, deformation, bending and/or manipulation locations for the therapeutic cushioning boot 100. According to certain embodiments, the first and second inner boundaries 120, 122 may be seams, including, for example, a threaded seam(s), radio frequency (RF) welded seam(s), or thermal fusion welded seam(s), among other types of seams, that extend through one or more layers of the body portion 102, such as, for example, inner and/or outer layers 124, 126 of the body portion 102. Further, according to certain embodiments, as also discussed below, the first and second inner boundaries 120, 122 may be adapted to contain and/or arrange the positioning of one or more types or concentrations of interior materials within at least certain regions of the body portion 102.

In the illustrated embodiment, the body portion 102 and the foot gate 104 may have an outer layer 126 that is operably connected to an inner layer 124. For example, according to certain embodiments, the inner and outer layers 124, 126 may be secured to each other by at least one or more seams that extend around at least a portion of the first outer edge 110, the second outer edge 112, the upper edge 106, and/or the lower edge 108. Additionally, according to certain embodiments, a single piece of material may, or may not, be used for the inner layer 124 for both the body portion 102 and the foot gate 104. Similarly, according to certain embodiments, a single piece of material may, or may not, be use for the outer layer 126 for both the body portion 102 and the foot gate 104. However, according to other embodiments, both the inner layer 124 and the outer layer 126 of the body portion 102 may be constructed from multiple pieces of material.

Additionally, the inner layer 124 and outer layer 126 may be formed from a variety of different materials. For example, according to certain embodiments, the inner layer 124 may be constructed from one or more types of fabric material, including, for example, a microfiber or a micro suede material, among other types of material, that provides a relatively comfortable surface for engagement with the skin of the user while also resistant to movement between the patients skin and the inner layer 124 so as to at least minimize the opportunity for such relative movement to generate friction that may damage the skin of the user or otherwise facilitate user discomfort. Conversely, according to certain embodiments, the outer layer 126 may be constructed using one or more materials that have a lower coefficient of friction than the inner layer 124. For example, according to certain embodiments, the outer layer 126 may be constructed from a nylon material, among other materials. Moreover, the material used for the outer layer 126 may allow for relatively easy sliding movement of the outer layer 126 of the therapeutic cushioning boot 100 along linen or other bedding materials with relatively low levels friction and/or shear forces.

Additionally, as discussed below, one or more interior regions of the body portion 102 and/or the foot gate 104 may contain one or more interior materials between the inner and outer layers 124, 126. Such interior materials 128a, 128b may be used for a variety of different purposes, including, for example, at least assisting in elevating the positioning of the foot and/or heel of the user when the a therapeutic cushioning boot 100 is operably positioned on a support surface, including, but not limited to, a bed, support board, or other support structure or apparatus, providing a cushioning or pillow effect, and/or providing support for the placement of the user's foot and/or the therapeutic cushioning boot 100, among other purposes. Advantageously, foot gate 104 (when open) allows a medical professional assess wounds, dissipate heat, and check offloading. In certain embodiments of boot 100, interior materials 128a, 128b are at least partially fibrous, and the fiber may include silicone.

According to certain embodiments, the foot gate 104 may include a top segment 130 and a bottom segment 132. The top segment 130 may include opposing front and rear edges 134a, 136a and opposing inner and outer surfaces 138a, 140a. Further, as shown in FIGS. 1 and 2, when the therapeutic cushioning boot 100 is in the open, unfolded condition, the top segment 130 may extend along a portion of the lower edge 108 so as to be adjacent to at least the first sidewall panel 114, and may also extend along a portion of the lower edge 108 that is adjacent to the rear panel 118. Similarly, the bottom segment 132 may also include opposing front and rear edges 134b, 136b and opposing inner and outer surfaces 138b, 140b. Further, when the therapeutic cushioning boot 100 is in the open, unfolded condition, the bottom segment 132 may extend along another portion of the lower edge 108 so as to be adjacent to at least the second sidewall panel 116, and may also extend along a portion of the lower edge 108 that is adjacent to the rear panel 118.

Figure 6:
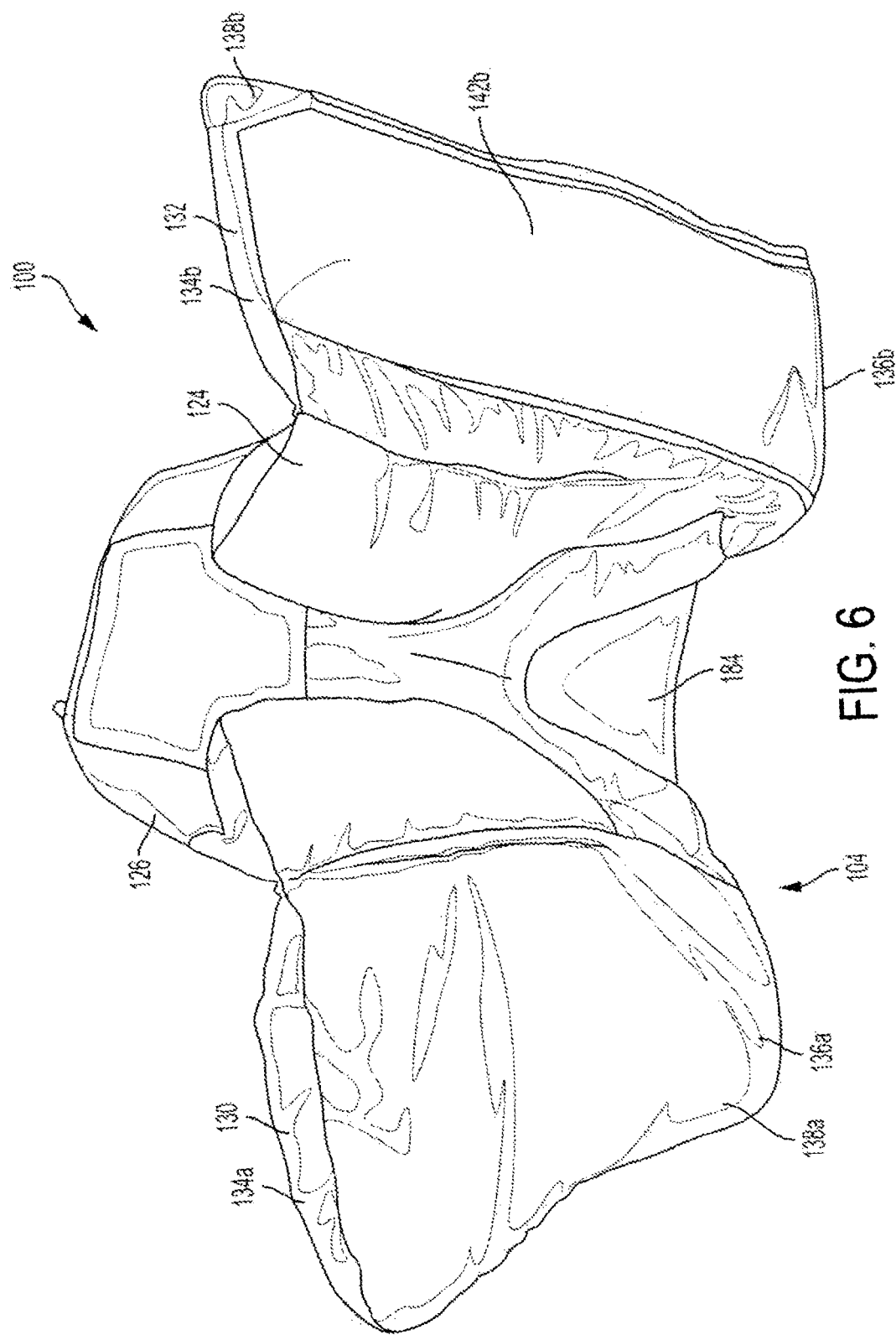
FIG. 6 illustrates a bottom perspective view of a therapeutic cushioning boot a body portion in a folded, closed condition and a foot gate in an open condition according to an illustrated embodiment of the present invention.
Figure 7:
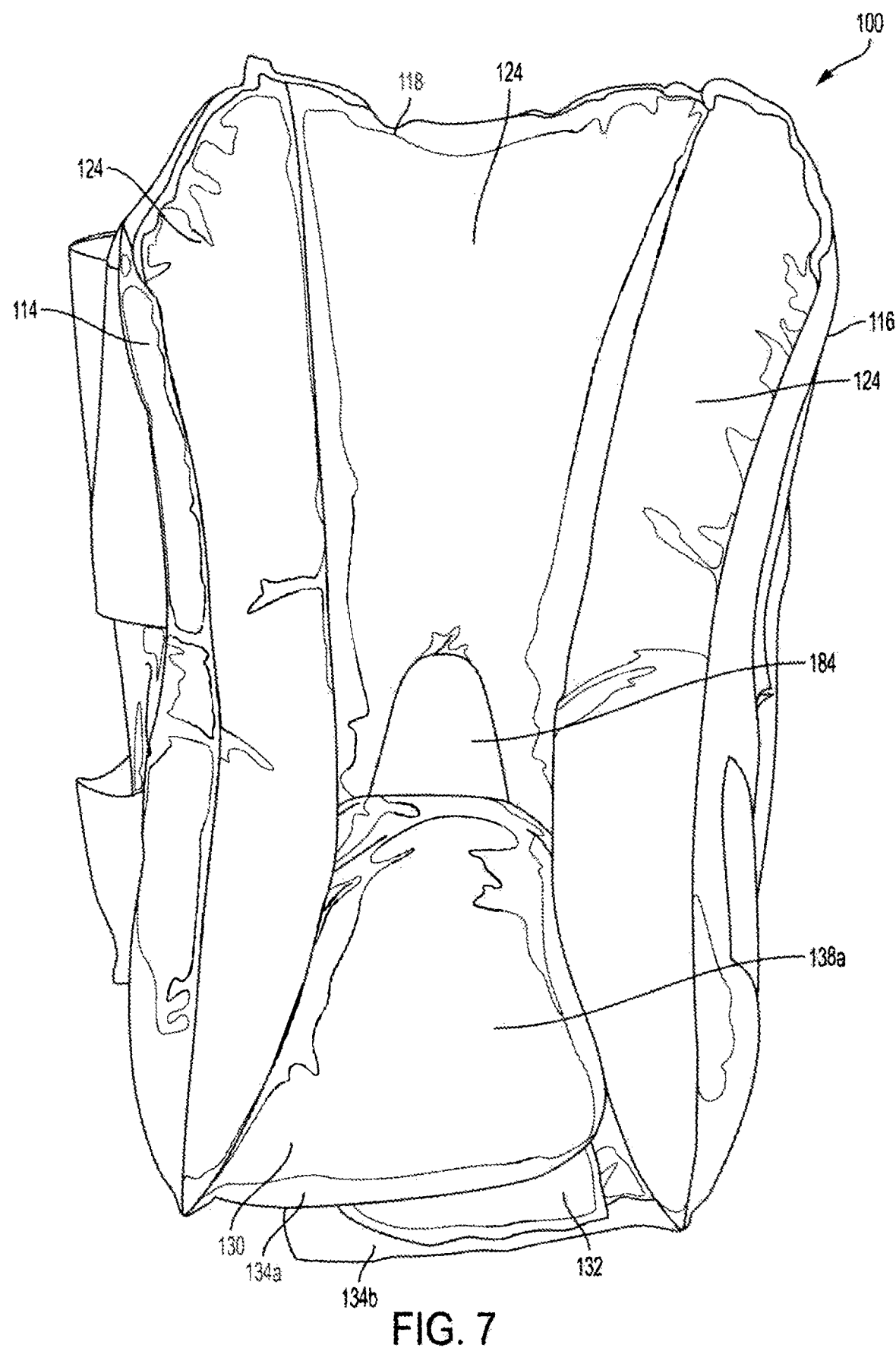
FIG. 7 illustrates a top view of a therapeutic cushioning boot in a folded and semi-closed condition according to an illustrated embodiment of the present invention.

As shown by at least FIG. 7, during usage of the therapeutic cushioning boot 100, the top segment 130 is configured to be folded, pivoted, or otherwise deformed or manipulated generally relative to at least the first sidewall panel 114 so that the inner surface 138a of the top segment 130 may be removably positioned adjacent to at least a portion of the bottom region of a user's foot. Additionally, the bottom segment 132 is configured to be folded, pivoted, or otherwise deformed or manipulated relative to at least the second sidewall panel 116 so that the bottom segment 132 may be removably secured to the top segment 130. For example, according to the illustrated embodiment, the top and bottom segments 130, 132 may be operably connected to each other at least when the therapeutic cushioning boot 100 is being secured to a user by one or more fasteners, such as, for hook and loop material, snaps, buttons, and/or a zipper, among other releasable connections. As shown in the embodiment depicted in FIGS. 1, 2, and 6, according to certain embodiments, the fastener may include a hook or loop fastener material 142a that is secured to a portion of the outer surface 140a of the top segment 130, while a portion of the inner surface 138b of the bottom segment 132 includes the other of the hook or loop fastener material 142b.

The ability to removably secure, and moreover, fully separate the top segment 130 from the bottom segment 132, including when the therapeutic cushioning boot 100 is operably secured to the user may provide a number of benefits, including, for example: the ability to manually adjust the width of the foot gate 104 to customize the width of the foot gate 104 for different patients or during different medical states or conditions; allow for relatively easy inspection of the bottom of the user's foot without having to entirely remove the therapeutic cushioning boot 100 and without the use of mirrors; allows for protection of the end of the user's foot, including the user's toes, as discussed below; and allows full passive range of motion. Further, the ability to fully open and close the foot gate 104 allows for visual inspection of the posterior aspect of the heel that may allow the clinician to visualize whether the heel is truly offloaded. Further, such a configuration of the foot gate 104 allows the boot 100 to be used in conjunction with an SCD device. Additionally, such a design allows for immediate inspection or venting of the foot without the need to lift the device off of the patient. Before this advancement, the only way to accomplish this was typically to lift the leg and completely remove the boot, which may subject the patient to unnecessary pain or disruption from a restful state. Further, the design of the foot gate 104, including the interior material contained therein, may allow for protection of the bottom of the foot from shearing forces in the seated patient, due to the inherent nature of the layered material at the foot gate 104. Additionally, by allowing the patient to have passive full range of motion may allow the patient to maintain flexibility of the joint and muscles. Passive range of motion also assists in muscular pump for venous blood flow return to heart.

According to the illustrated embodiment, the front edge 134a, 134b of at least one of the top and bottom segments 130, 132 may be separated from the rear edge 136a, 136b by a distance (as indicated by dl in FIG. 2) that allows the front edge 134a, 134b to extend beyond the end of a user's foot, such as, for example, for at least certain users, beyond the user's toes. Moreover, the front edge 134a, 134b of either or both of the top segment 130 and the bottom segment 132 extend beyond the end of the foot that is positioned in the therapeutic cushioning boot 100, and thereby prevent or minimize exposure of the end of the user's foot to a variety of different types of trauma and/or pressure. For example, by extending the front edge 134a, 134b of the top and/or bottom segments 130, 132 beyond the end of a user's foot that is positioned in the therapeutic cushioning boot 100, the front edge 134a, 134b may prevent linens and/or blankets from resting against the end of the user's foot, and thereby protect the end of the user's foot from prolong exposure to the associated pressure of such blankets and linens. Additionally, by configuring the front edge 134a, 134b of the top segment 130 and/or and the bottom segment 132 to extend beyond the end of the user's foot, that front edge 134a, 134b may protect the end of the user's foot from contact with other structures, such as, for example, shielding the user's toes from contact with a bed frame, door, and/or wall as the user is transported in a wheel chair. According to certain embodiments, the distance (dl) between one or both of the respective front and rear edges 134a, 136a, 134b, 136b may be configured for the front edge 134a, 134b to extend at least one-half inch to two inches beyond the end of the user's foot, including toes (if applicable). Such numerical ranges however are exemplary, and may vary for different embodiments and patient anatomies.

According to certain embodiments, the first and second sidewall panels 114, 116 may each include an upper region 144 and a lower region 146 that are positioned between adjacent portions of the opposing upper and lower edges 106, 108. The upper region 144 of the first and second sidewall panels 114, 116 may be configured to be secured to, or otherwise wrapped about, at least a portion of the lower leg of the user, such as, for example, about at least a portion of the user's leg that is at least below the user's knee and above a foot and/or ankle. For example, referencing FIGS. 1 and 3, the upper region 144 of the first and second sidewall panels 114, 116 may include an upper fastener 148 that secures at least the upper regions 148 of the first and second sidewall panels 114, 116 about a calf region of the user's leg. Moreover, for example, in the illustrated embodiment, the upper region 144 of either the first or second sidewall panels 114, 116 may include an upper fastener 148 that is operably secured to the other of the upper region 144 of the first or second sidewall panels 114, 116, such as for example by an upper fastener 148 on that mates a hook or loop material of the upper fastener strip 150. According to certain embodiments, the upper fastener 148 may have a generally rectangular shape with a width of approximately 6 inches.

Similarly, the lower region 146 may be configured to be secured to, or otherwise wrapped about, at least a portion of a foot of the user. Moreover, the lower region 146 may be sized to be positioned about at least a portion of the sides of the user's foot. Further, according to certain embodiments, the lower region 146 may also be sized to cover at least a portion of an upper surface of a user's foot when the therapeutic cushioning boot 100 is operably secured to the user. Further, in the illustrated embodiment, the lower region 146 of either of the first or second sidewall panels 114, 116 may include a lower fastener 152 that is operably secured to the other of the lower region 146 of the first or second sidewall panels 114, 116, such as for example a lower fastener 152 that mates a hook or loop material of the lower fastener strip 154. According to certain embodiments, the lower fastener 152 may have a generally rectangular shape with a width of approximately 3.5 inches.

The lower region 146 of the either or both of the first or second sidewall panels 114, 116 may also include an access port 156 that is configured to permit the passage of instrumentation, such as, for example, tubing out of, or into, a folded, closed therapeutic cushioning boot 100. The access port 156 may have a variety of shapes and sizes, including, for example, being generally rectangular. Further, according to the illustrated embodiment, the access port 156 may be spaced away from at least the adjacent first or second inner boundary 120, 122 to prevent kinking of tubing that may be exiting the therapeutic cushioning boot 100 through the access port 156.

According to the depicted embodiment, with the exception of the inclusion of a chamfered edge 158, according to the illustrated embodiment, the first and second outer edges 110, 112 along the upper region 144 of the first and second sidewall panels 114, 116 may be generally parallel to the first and second inner boundaries 120, 122, respectively. Further, as shown in FIGS. 1 and 2, when the therapeutic cushioning boot 100 is in an open and flattened condition, the first and second outer edges 110, 112 and the first and second inner boundaries 120, 122 may be generally parallel to a central axis 160 of the therapeutic cushioning boot 100. Thus, according to certain embodiments, the upper region 144 may have a relatively uniform first width, as indicated by w1 in FIG. 2. Such widths of the upper regions 144 of the first and second sidewall panels 114, 116 may be configured to allow the therapeutic cushioning boot 100 to encompass at least a portion of the side surfaces of a user's lower leg.

Again referencing FIGS. 1 and 2, as the first and second outer edges 110, 112 transition from the upper regions 148 to the lower regions 146, the first and second outer edges 110, 112 may extend outwardly away from at least the first and second inner boundaries 120, 122, respectively, so as to attain a second width along, or in the vicinity of, at least the lower edge 108, as indicated by w2 in FIG. 2. For example, as shown in FIGS. 1 and 2, the first and second outer edges 110, 112 along the lower regions 146, respectively, may extend away from at least the first and second inner boundaries 120, 122 such that at least a portion of the outer edge 110, 112 is generally aligned with the front edge 134a, 134b of the adjacent top or bottom segment 130, 132 of the foot gate 104. Thus, according to such embodiments, similar the front edges 134a, 134b of the top segment 130 and/or bottom segment 132, the lower region 146 of the first and second sidewall panels 114, 116 may also be configured to prevent or minimize exposure of the end of the user's foot to a variety of different types of trauma and/or pressure.

Figure 4:
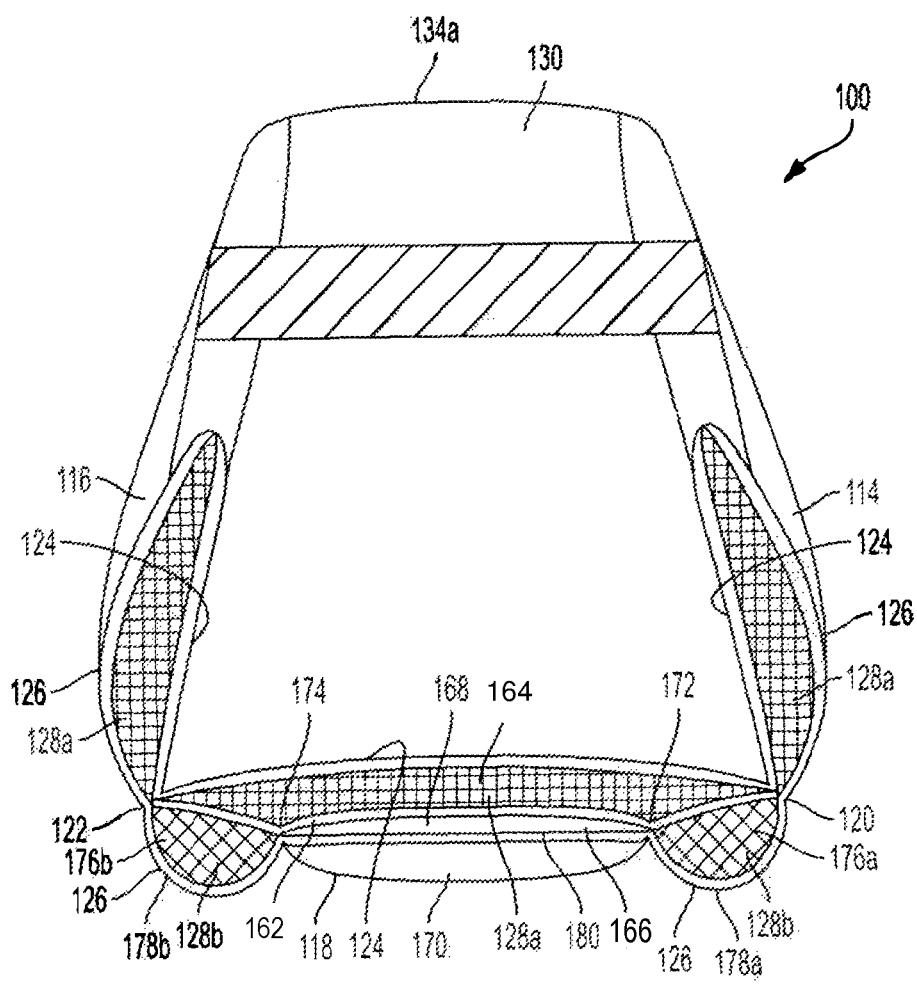
FIG. 4 illustrates a cross sectional view of a portion of a therapeutic cushioning boot taken along line A-A in FIG. 3.
Figure 5:
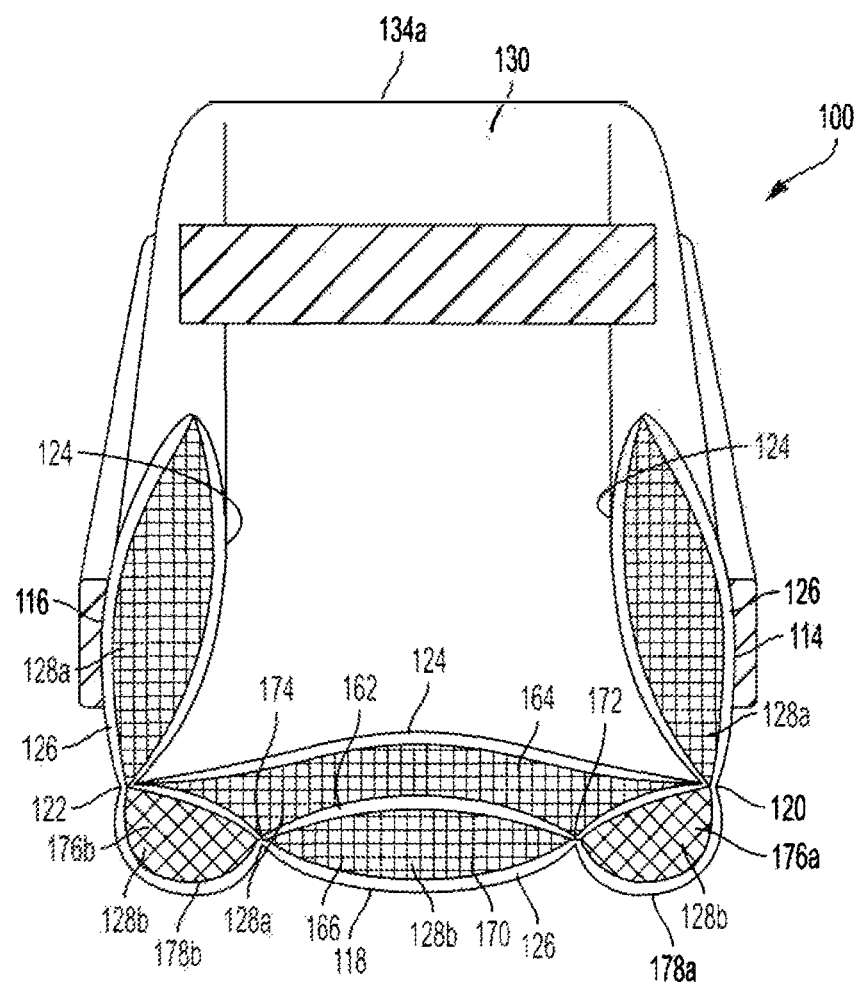
FIG. 5 illustrates a cross sectional view of a portion of a therapeutic cushioning boot taken along line B-B in FIG. 3.

Referencing FIG. 1, according to the illustrated embodiment, the rear panel 118 may be positioned between the first and second sidewall panels 114, 116. Additionally, as shown by at least FIGS. 4 and 5, at least a portion of the outer layer 126 and the inner layer 124 may be separated by at least an intermediate layer 162. Moreover, the intermediate layer 162 may be positioned to provide a divider between first and second segments 164, 166 of the rear panel 118, with the first segment 164 being positioned between the inner layer 124 and the intermediate layer 162 and the second segment 166 being positioned between the outer layer 126 and the intermediate layer 162. As shown in FIGS. 4 and 5, the first segment 164 may extend between the intermediate layer 162 and inner layer 124 from the first and second inner boundaries 120, 122. As further illustrated by at least FIGS. 4 and 5, when the therapeutic cushioning boot 100 is in the closed, folded condition, the first and second sidewall panels 114, 116 may be folded over at least a portion of the rear panel 118 such that the seam for the first and second inner boundaries 120, 122 along the inner layer 124 or inside portion of the closed, folded therapeutic cushioning boot 100 recessed and/or covered by the first and second sidewall panels 114, 116, thereby preventing or minimizing the opportunity for the seam of the first and second inner boundaries 120, 122 to be an irritant to the skin or tissue of the user's leg. Further, as also shown by FIGS. 4 and 5, according to the illustrated embodiment the rear panel 118 may, or may not, contain another seam along the inner layer 124 between the first and second inner boundaries 120, 122. However, according to certain embodiments, the rear panel 118 may not include such a seam between the first and second inner boundaries 120, 122, as such a seam may potentially create a source for an irritant for the user. Further, according to the illustrated embodiment, the first segment 164 may contain a first interior material 128a that is sized to prevent folding or kinking of the inner layer 124 along the rear panel 118, and thereby also at least attempt to prevent the formation of an irritant along the inner layer 124 of the rear panel 118. Additionally, the first interior material 128a used in the first segment 164, such as, for example, polyester fiberfill, may again be a material that provides a cushion or pillow effect or sensation for the user, particularly the user's calf region.

Figure 9:
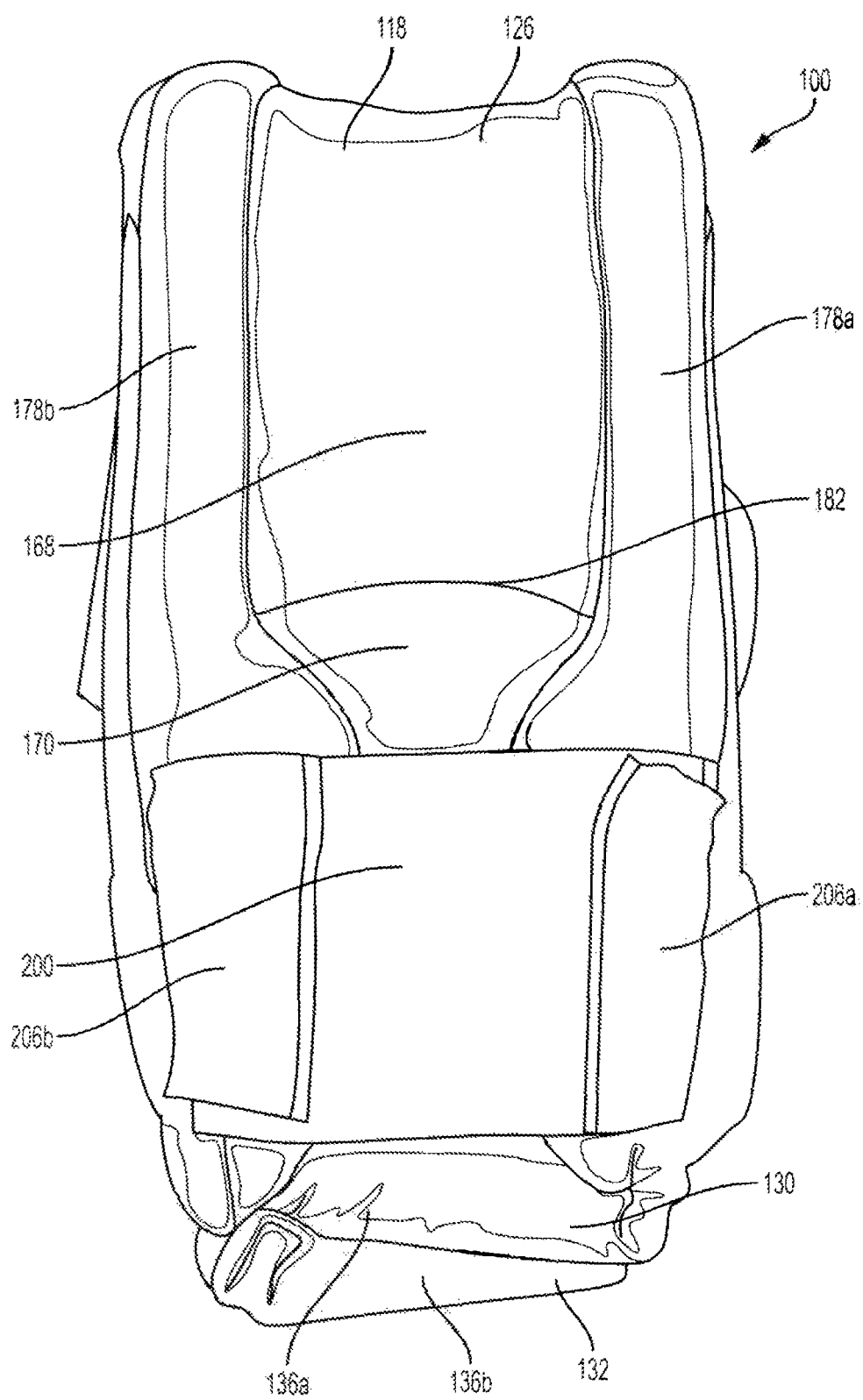
FIG. 9 illustrates a rear view of a therapeutic cushioning boot in a folded and closed condition and emphasizing a pair of support sleeves according to an illustrated embodiment of the present invention.

The second segment 166 may be configured to provide at least one or more support chambers 168, and an elevation chamber 170. According to certain embodiments, the first support chamber 178a may be positioned between the first inner boundary 120 and a first support boundary 172, while the second support chamber 178b may be positioned between the second inner boundary 122 and a second support boundary 174. Referencing FIG. 4, according to certain embodiments, the first and second support boundaries 174, 176 may each be provided by seams that operably connect at least the outer layer 126 to the intermediate layer 162. Further, the first and second support boundaries 174, 176 may be offset from the first and second inner boundaries 120, 122, respectively, so as to provide a recesses 176a, 176b there between that may be filled with a second interior material 128b. The second interior material 128b may provide a degree of stiffness and/or rigidity to first and second support chambers 178a, 178b that at least assists in preventing twisting or turning of the therapeutic cushioning boot 100 when at least a portion of the rear panel 118 is positioned against an adjacent support structure, such as, for example, a bed. According to certain embodiments, the second interior material 128b may be a stiffer and/or more rigid material than the first interior material 128a, or be the same material as the first interior material 128a but provided in a greater quantity or concentration in the given space, such as, for example, by overfilling or hyper-stuffing the second interior material 128b into the recesses 176a, 176b. Referring also to FIG. 9, in certain embodiments of boot 100, first and second support chambers 178a, 178b define a pair of stabilizing rails disposed in parallel on the exterior rear of the boot 100.

According to certain embodiments, the first and second support chambers 178a, 178b are overstuffed regions on the underside of the rear panel 118 that have enlarged portions at the foot end of the therapeutic cushioning boot 100 that prevent rotation, give rigidity, provide heel lifting height and center the recessed area at the Achilles tendon. Further, rather than over or hyper stuffing the first and second support chambers 178a, 178b, an insert preformed and cut to size may be insert into the first and second support chambers 178a, 178b. Further, the first and second support chambers 178a, 178b may: prevent lateral rotation from small torsional forces; provide rigidity to allow the product to freely sit upright without external supports; provides consistent heel lifting height to allow a softer pillow in the upper chamber; and, create a recessed center portion to cradle the Achilles tendon and allow complete offloading of the posterior heel when in bed. Further, unlike traditional devices that often tend to not have a boot sit upright, such use of the first and second support chambers 178a, 178b of the present invention may position the leg with the hip in neutral alignment with the patient at rest, and thus the first and second support chambers 178a, 178b may allow the therapeutic cushioning boot 100 to sit upright in order to aid the clinician when placing the therapeutic cushioning boot 100 on the patient's/user's leg. The therapeutic cushioning boot 100 may also provide heel lifting height from bed surface to offload pressure at the posterior heel and allows the upper chamber to be softer and more comfortable and allow for less bulk along the upper chamber which places the leg closer to the adjacent support surface, such as, for example, the adjacent bed surface or a support board, preventing potential hyperextension forces at the knee. The first and second support chambers 178a, 178b may also provide a cradle for the Achilles tendon to be comfortably offloaded due to the recessed center portion.

Referencing FIGS. 4 and 5, the second segment 166 may include a first chamber 180 that is positioned between the first and second support chambers 178a, 178b, and between a portion of the upper edge 106 and the elevation chamber 170. In the illustrated embodiment, the first chamber 180 may not include first or second interior material 128a, 128b, or may have a minimal amount of such interior materials 128a, 128b so as to prevent the therapeutic cushioning boot 100 from being tilted in a downward position when the rear panel 118 is positioned on a relatively flat surface.

Referencing FIGS. 1 and 5, the elevation chamber 170 may be separated from the first chamber by at least a chamber boundary 182. For example, in the illustrated embodiment, the chamber boundary 182 may be a seam that assists in retaining the selected interior material 128a, 128b in the elevation chamber 170. According to certain embodiments, the elevation chamber 170 may contain a second interior material 128b that may, again, be a more rigid or stiffer material than the first interior material 128a, or may be same material as the first interior material 128a, but provided in greater quantity or concentration in the given space, such as, for example, by overfilling or hyper-stuffing the second interior material 128b into the elevation chamber 170.

Referencing at least FIGS. 1, 2, 6, and 7, according to the illustrated embodiment, at least a portion of the lower edge 108 along the rear panel 118 is configured to provide a relatively deep "V" shaped opening 184 that is cut in the rear panel 118 that generally extends from the lower edge 108 toward the upper edge 106. Further, the "V" shaped opening 184 may be sized for at least a portion of the user's heel to extend out of the therapeutic cushioning boot 100 through the "V" shaped opening 184. For example, as shown in FIG. 1, according to the illustrated embodiment, a portion of the lower edge 108 on the first sidewall panel 114 side of the central axis 160 may have a first leg 186 that angularly and inwardly extends from the lower edge 108 toward the central axis 160. Similarly, according to the illustrated embodiment, a portion of the lower edge 108 on the second sidewall panel 116 side of the central axis 160 may have a second leg 188 that angularly and inwardly extends from the lower edge 108 toward the central axis 160 in a direction that is generally opposite of to the first leg 186. Further, according to the illustrated embodiment, the first and second legs 186, 188 may be joined by a curved section 190 of the "V" shaped opening 184. Further, the first and second legs 186, 188 may be separated at mouth portion of the "V" shaped opening 184 that has a width (as indicated in FIG. 2 as w3) that is larger than a depth of the "V" shaped opening 184 at an apex location of the curved section 190 (as indicated by d3 in FIG. 2). The difference between the width (w3) to the depth (d3) of the "V" shaped opening 184 may vary according to embodiments. For example, according to certain embodiments, the width (w3) to depth (d3) ratio of the "V" shaped opening 184 may be 2:1.

According to certain embodiments, the "V" shaped opening 184 is a heel well that is cut to a depth (d3) of four inches and a width (w3) of six inches. Further, the "V" shaped opening 184 may be configured to offload the heel and/or Achilles tendon while also allowing for motion without causing shear forces on the heel or Achilles tendon area. Moreover, the "V" shaped opening 184 may place the posterior heel in an offloaded position by eliminating material underneath the heel and places the Achilles tendon in an offloaded position by eliminating material underneath the Achilles tendon area. The "V" shaped opening 184 may also prevent shearing and/or frictional forces at the posterior heel or Achilles tendon area with ankle mobility due to the offloading in these areas.

Figure 8:
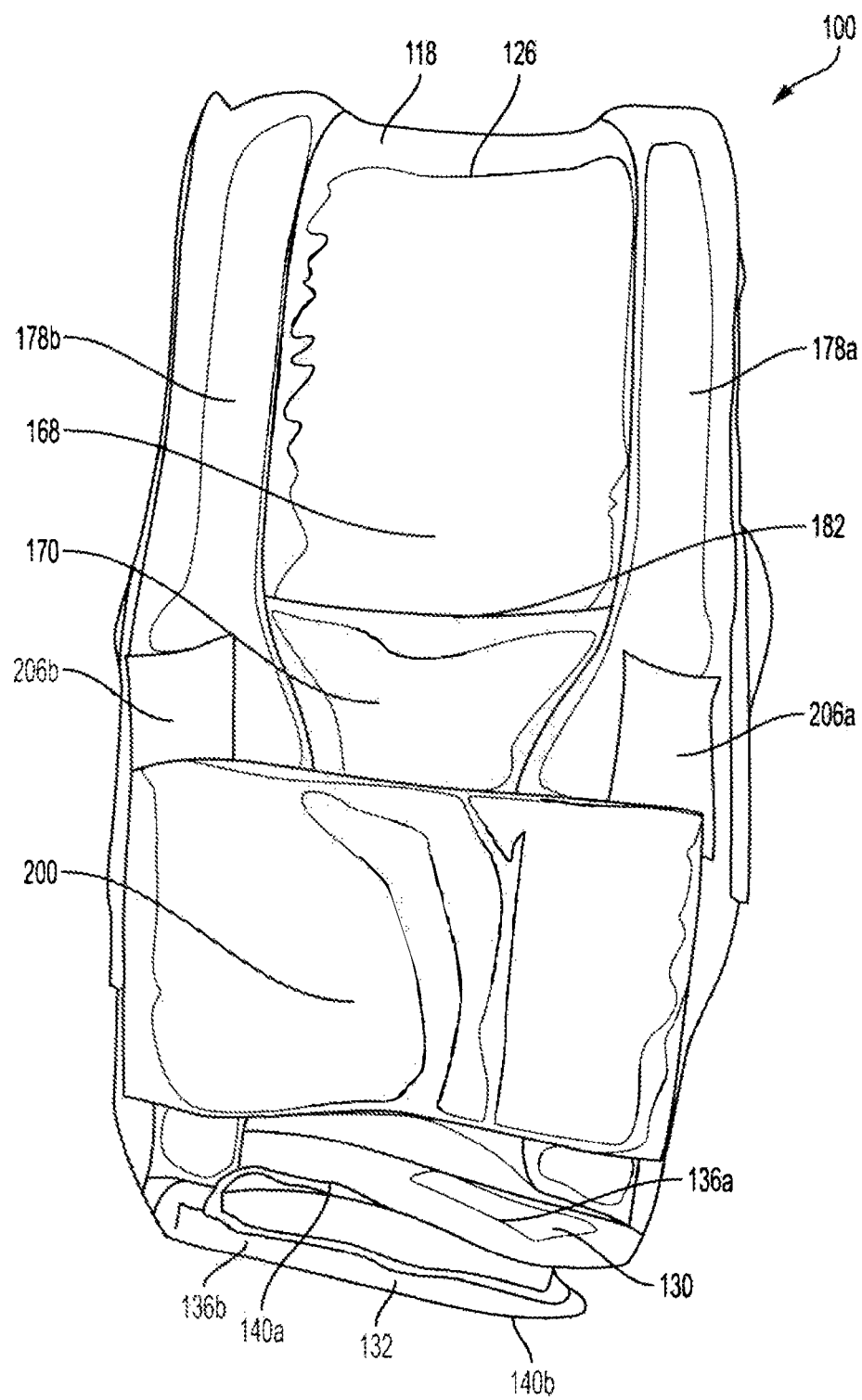
FIG. 8 illustrates a bottom view of a therapeutic cushioning boot in a folded and closed condition according to an illustrated embodiment of the present invention.

As shown in at least FIGS. 1 and 8, according to certain embodiments, the rear panel 118 may be operably connected to an anti-shear barrier 200. According to certain embodiments, the anti-shear barrier 200 may be a fabric having a relatively low coefficient of friction. Moreover, according to certain embodiments, the anti-shear barrier 200 is a taut piece of fabric, such as, for example, nylon, that may or may not include padding that is sewn into boot side seams under heel well. Alternatively, rather than being sewn into the boot 100, according to other embodiments, the anti-shear barrier 200 is removably secured to the boot 100, such as, for example, via the use of a fastener(s), including, but not limited to, hook and loop material, buttons, snaps, and zippers, among other devices. According to the illustrated embodiment, the anti-shear barrier 200 may be a nylon material. According to the embodiment depicted in FIG. 1, the anti-shear barrier 200 is operably connected to the outer layer 126. For example, first and second ends 202, 204 of the anti-shear barrier 200 may be operably secured to at least the rear panel 118 at the first and second inner boundaries 120, 122. However, according to certain embodiments, rather than being positioned adjacent to the outer layer 126 at the rear panel 118, according to other embodiments, the anti-shear barrier 200 may be positioned adjacent to the inner layer 124 along the rear panel 118. Further, according to the illustrated embodiment, the anti-shear barrier 200 may be positioned to cover at least a portion of the "V" shaped opening 184 so that, when the therapeutic cushioning boot 100 is operably secured to a user, the antishear barrier 200 covers at least a portion of the user's heel. Moreover, by covering the "V" shaped opening 184, the anti-shear barrier 200 may provide a low friction surface that generally shields or minimizes the amount of friction that the heel of the user may experience as the heel abuts or moves against an adjacent surface, such as, for example, along bed linen and/or a support board. Moreover, the anti-shear barrier 200 may provide static contact to heel in order to prevent shearing and/or frictional forces when sliding the heel up or down in bed.

Figure 10:
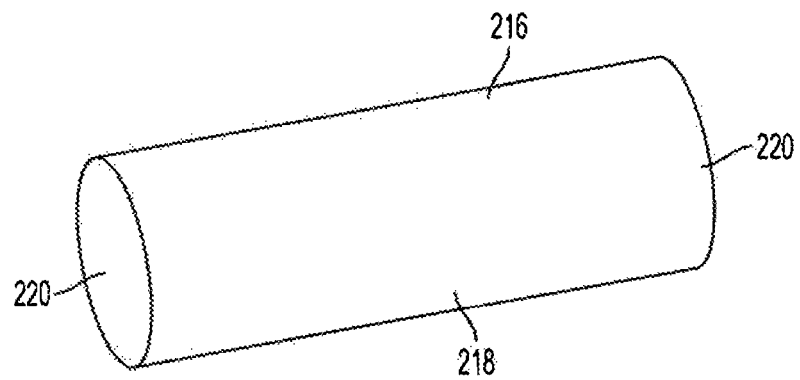
FIG. 10 illustrates a side perspective view of a support device having a generally elongated cylindrical configuration according to an illustrated embodiment.
Figure 11:
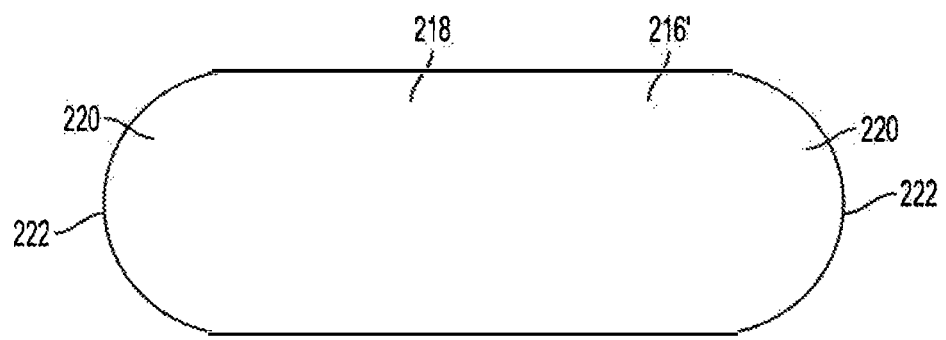
FIG. 11 illustrates a side view of a support device having a countered outer edge to facilitate at least insertion of the support device into a support sleeve.

As shown in at least FIGS. 1 and 9, according to certain embodiments, the rear panel 118 may also include one or more support sleeves 206a, 206b. The support sleeves 206a, 206b may provide retention areas for the removable insertion of support devices 216, 216', 216" shown, for example, in FIGS. 10, 11, and 12, that may at least assist in maintaining the position of the therapeutic cushioning boot 100 when in use. Moreover, the support devices 216, 216', 216" may assist in preventing the supported calf, ankle, and/or foot from twisting or turning, and instead at least the outer layer 126 of the rear panel 118 against an adjacent surface, such as, for example, against an adjacent bed surface or support board. Moreover, the support sleeves 206a, 206b may be positioned to at least assist in retaining the foot of the user in a generally upright, or nontwisted, position.

Figure 12:
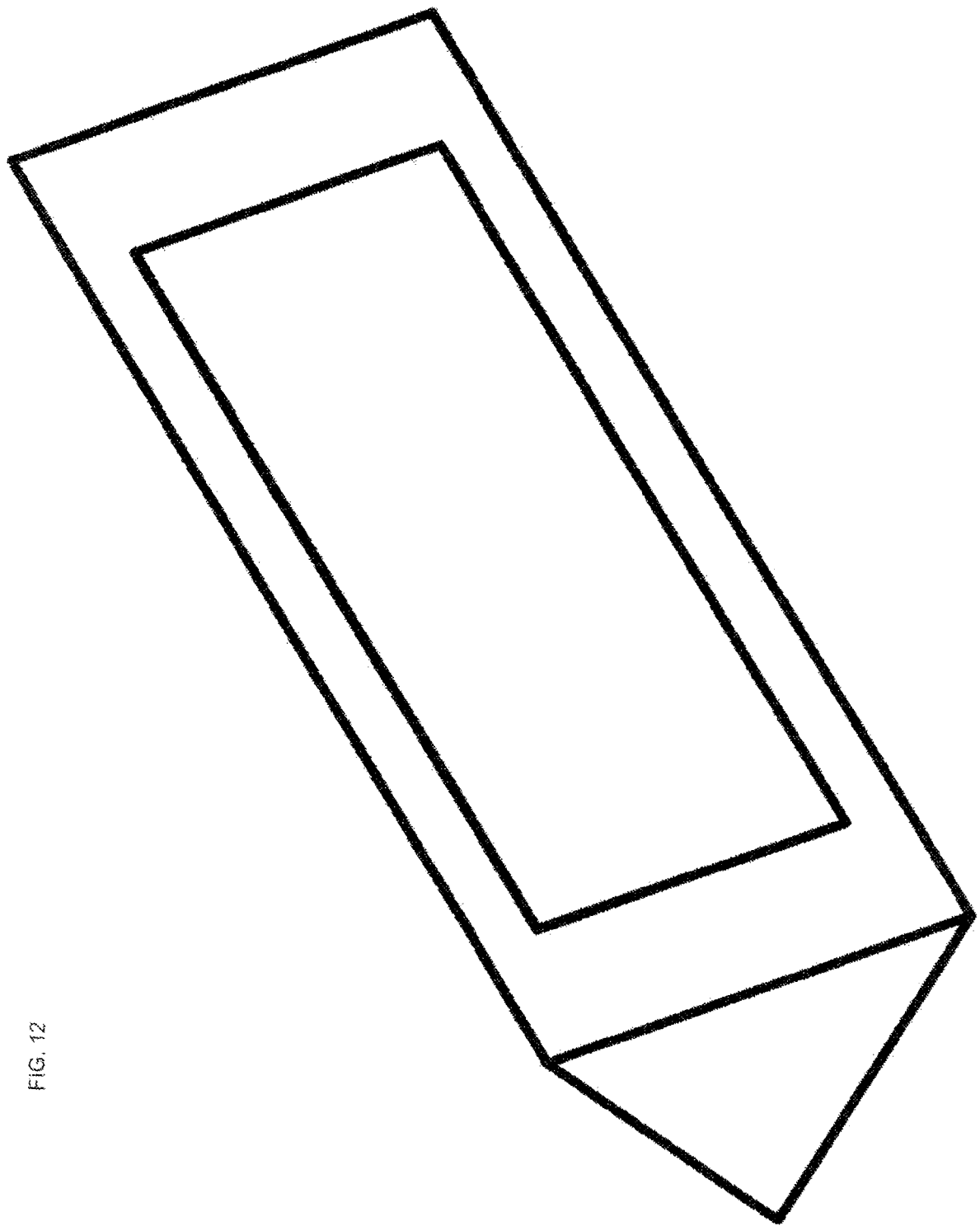
FIG. 12 illustrates a side perspective view of a support device according to an exemplary embodiment that is generally configured as a triangular prism.

The support sleeves 206a, 206b may be made of a variety of different materials and have a variety of shapes and/or configurations. For example, according to the illustrated embodiment, the support sleeves 206a, 206b may be an elastic or non-elastic material that is arranged in a cylindrical configuration having an aperture that is sized to receive the insertion of a support device. Additionally, the support devices 216, 216', 216" may also have a variety of shapes and configurations. For example, according to certain embodiments, the support devices 216, 216' may have a generally cylindrical shaped body segment 218 that is sized for removable insertion into the support sleeves 206a. 206b. For example, according to certain embodiments, the support devices 216 may be generally six inches in length and have a diameter of approximately one to two inches. Further, referencing FIG. 11, according to certain embodiments, at least one end 220 of the support devices may have a tapered or contoured surface 222 that is configured to facilitate insertion of the support device into the associated support sleeves 206a, 206b. Alternatively, as shown in FIG. 12, support device 216" may comprise an extruded pyramid shape defining a triangular prism.

According to certain embodiments, the support sleeves 206a, 206b may be a taut piece of fabric, similar to Lycra, that is attached to opposing sides of the elevation chamber 170 and which allows for the placement of a cylindrically shaped support device 216 to prevent the foot or hip from rotating. Further, the support sleeves 206a, 206b may be used with the support devices 216 to avoid external rotation of the hip, to avoid internal rotation of the hip, and to eliminate the usage of wedges. Additionally, insertion of the support devices 216 may be optional, and in at least some circumstances the support devices 216 may not be used. Further, use of the support sleeves 206a, 206b with the support devices 216 may allow for the supine patient to be protected from rotational forces at the hip, yet the support devices 216 can easily be removed from the support sleeves 206a, 206b when the patient is in a side lying position. Further, unlike the support devices 216 of the present invention, other, more bulky wedge devices may place the side lying patient in an abnormal position or cause unnecessary rotational forces at the hip or knee. Additionally, the support sleeves 206a, 206b and support devices 216 of the present invention prevents rotation of hip which can otherwise cause misalignment, excessive stress and/or pain at the hip.

Figure 3:
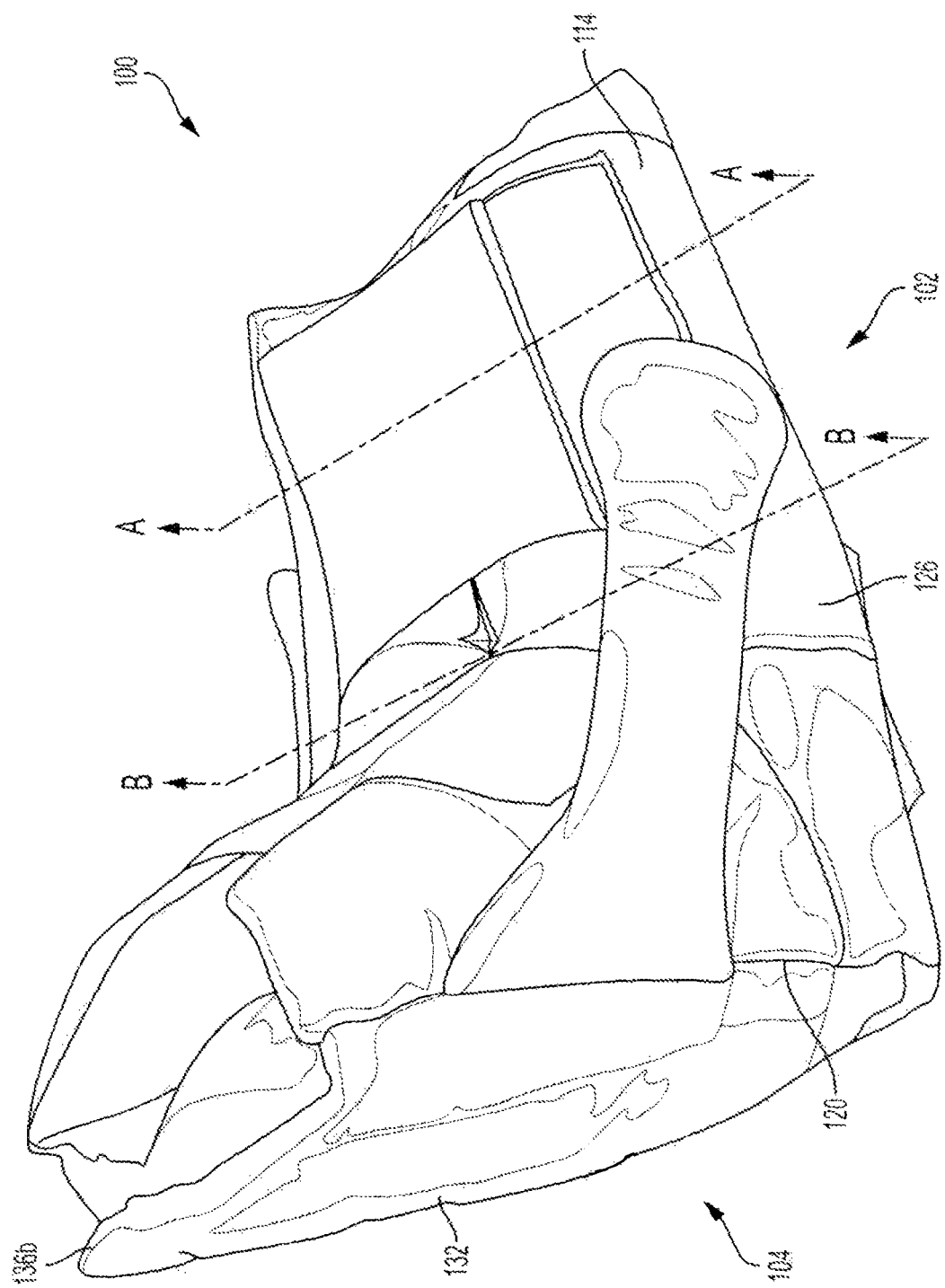
FIG. 3 illustrates a first side perspective view of a therapeutic cushioning boot in a closed, folded condition according to an illustrated embodiment of the present invention.

Additionally, as shown in at least FIGS. 1 and 3, the therapeutic cushioning boot 100 may also include one or more retention straps 208a, 208b. According to the illustrated embodiment, the retention straps, 208a, 208b may be straps of material that are adapted to at least retain the foot at a particular, adjustable position, and/or to prevent the position of the foot from dropping. Further, according to the illustrated embodiment, the retention straps 208a, 208b have a first end 210 and a second end 212, the first end 210 having either a hook or loop material that mates the hook or loop material of the adjacent upper fastener element 214. The second end 212 of at least a first retention strap 208a may be operably secured to at the lower edge 108 between the first sidewall panel 114 and the top segment 130, while the second end 212 of at least a second retention strap 208b may be operably secured to at the lower edge 108 between the second sidewall panel 116 and the bottom segment 132. Additionally, the second ends 212 of the first and second retention straps 208a, 208b may be secured at the lower edge 108 at positions that generally translate to a mid-section or central location of the user's foot. Such positioning of the second end 212 of the first and second retention straps 208a, 208b may prevent the first and second retention straps 208a, 208b from facilitating a bending or twisting force directed at an upper region of the user's foot. When used, the first and second retention straps 208a, 208b may be pulled so as to position the user's foot in a generally upright position. Moreover, the pulling of the first and second retention straps 208a, 208b may pull the foot gate 104 so that the foot gate 104 is generally perpendicular to the rear panel 118. The foot gate 104 may then be secured in the pulled position by securing the first end 210 of the pulled first and second retention straps 208a, 208b to the upper fastener element 214 of the first or second sidewall panels 114, 116, respectively.

According to certain embodiments, the retention straps 208a, 208b are straps can be pulled to varying degrees of tightness and attached via hook and loop, among or other types of fastening methods, to the side of the boot 100. According to certain embodiments, the outer surfaces of the retention straps 208a, 208b are constructed from a nylon material and enclose a first interior material 128a, such as, for example, a foam pad. According to certain embodiments, the retention straps 208a, 208b straps are positioned on either side of foot gate 104, thereby eliminating the potential for pressure along the bottom of the foot. Unlike embodiments of the present invention, other products incorporate straps along the entire weight bearing surface of the foot, near the toes, which may facilitate the potential for developing pressure points. Further, the retention straps 208a, 208b of the present invention allow the clinician to position the ankle in neutral without the potential for ulcer development along the weight bearing surface of the foot.

Figure 13:
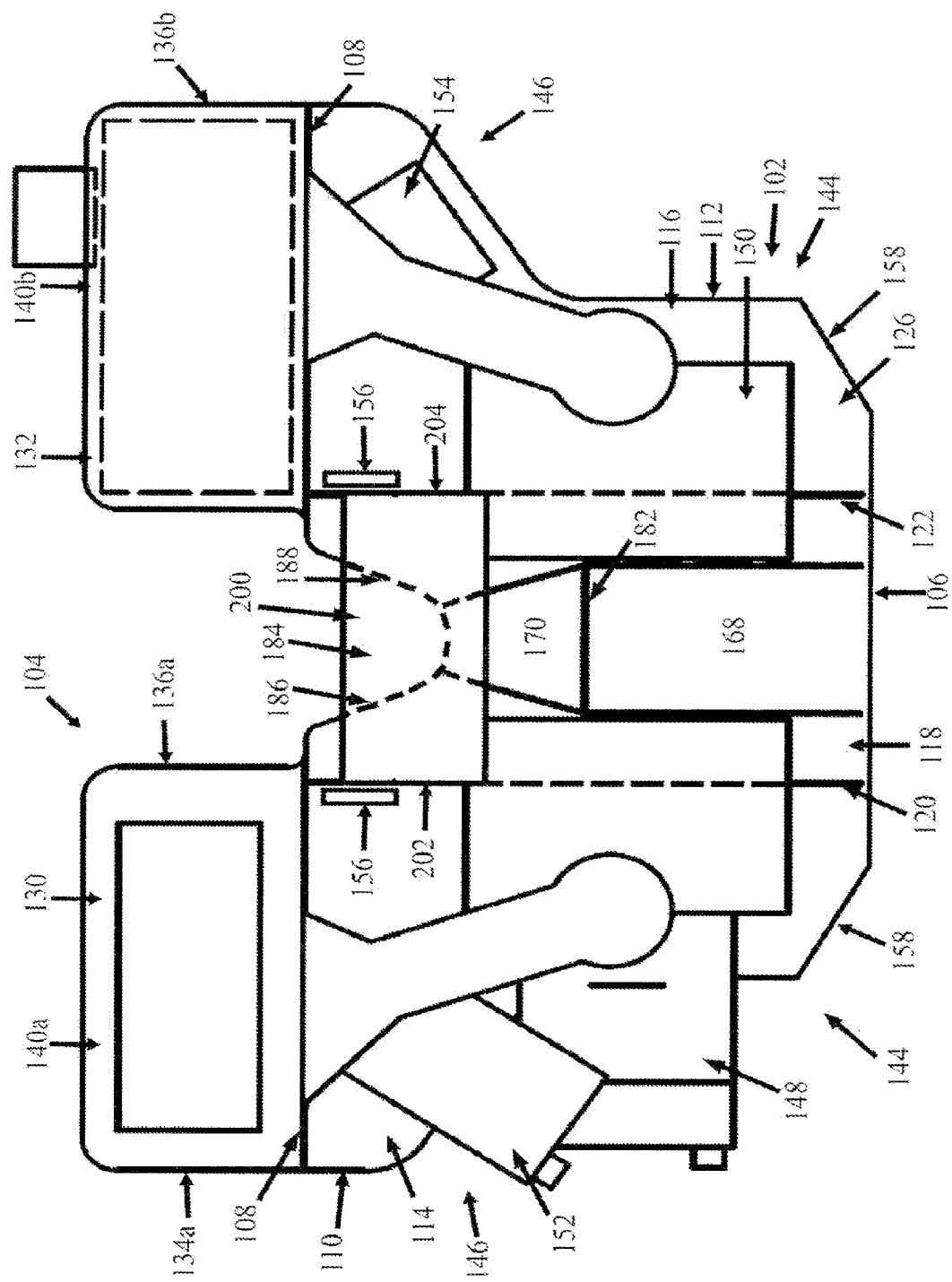
FIG. 13 illustrates an outside view of a therapeutic cushioning boot in an open and flattened condition according to an alternative illustrated embodiment of the present invention.
Figure 14:
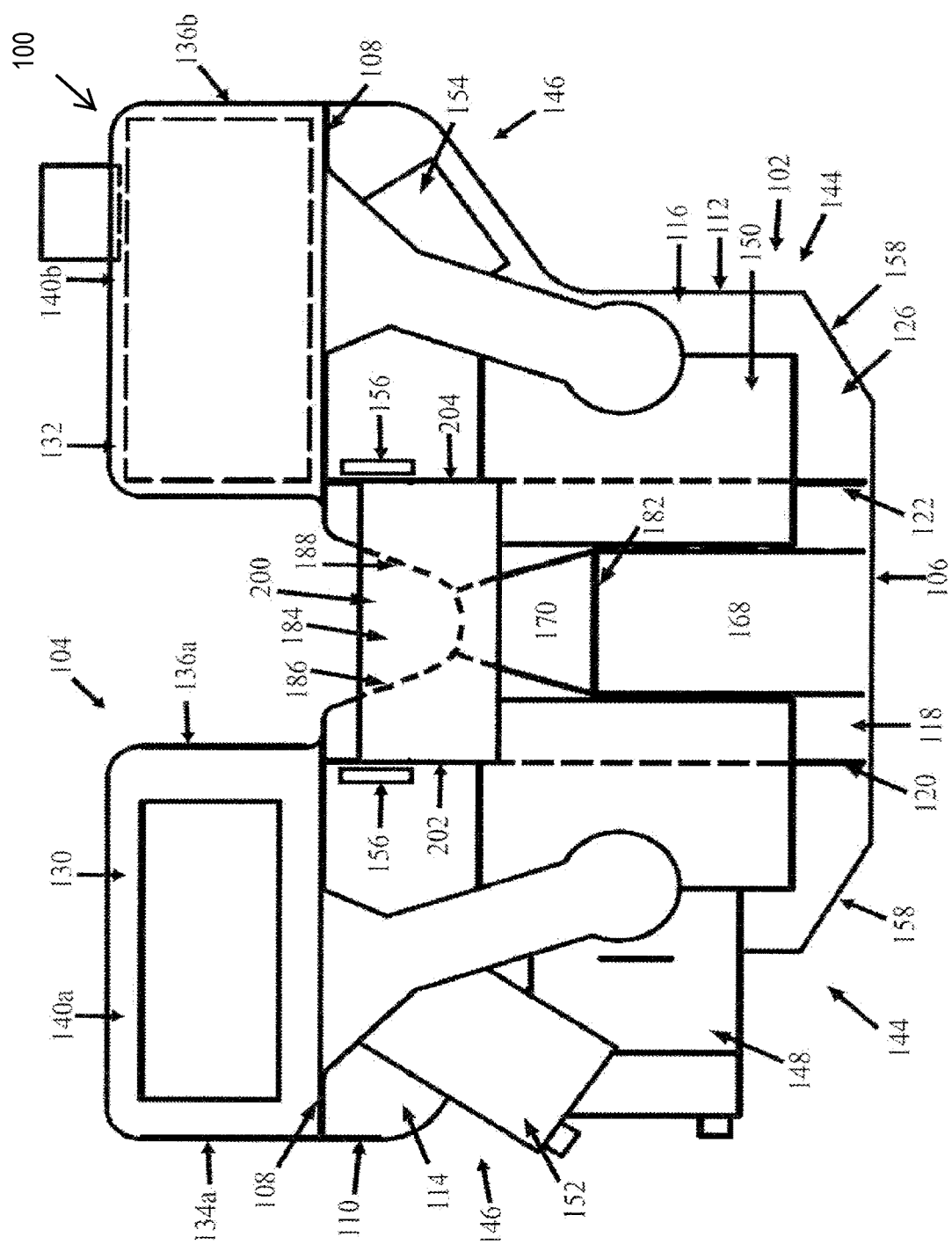
FIG. 14 illustrates an inside view of the therapeutic cushioning boot shown in FIG. 13.

FIGS. 13 and 14 illustrate outside and inside views, respectively, of an alternative exemplary embodiment of a therapeutic cushioning boot 100 in an open and flattened condition, such as, for example, before the therapeutic cushioning boot 100 has been operably positioned about at least a portion of a lower leg region and/or foot of the user. In the illustrated embodiment, the therapeutic cushioning boot 100 may include a body portion 102 and a foot gate 104. The body portion 102 may include an upper edge 106, a lower edge 108, a first outer edge 110, and a second outer edge 112. Additionally, according to the illustrated embodiment, the body portion 102 may include a first sidewall panel 114, a second sidewall panel 116, and a rear panel 118. The first sidewall panel 114 may extend from the first outer edge 110 to a first inner boundary 120, while the second sidewall panel 116 may extend from the second outer edge 112 to a second inner boundary 122. The rear panel 118 may extend between the first and second inner boundaries 120, 122. According to certain embodiments, as discussed below, the first and second inner boundaries 120, 122 may provide pivot, deformation, bending and/or manipulation locations for the therapeutic cushioning boot 100. According to certain embodiments, the first and second inner boundaries 120, 122 may be seams, including, for example, a threaded seam(s), radio frequency (RF) welded seam(s), or thermal fusion welded seam(s), among other types of seams, that extend through one or more layers of the body portion 102, such as, for example, inner and/or outer layers 124, 126 of the body portion 102. Further, according to certain embodiments, as also discussed below, the first and second inner boundaries 120, 122 may be adapted to contain and/or arrange the positioning of one or more types or concentrations interior materials within at least certain regions of the body portion 102.

Again referencing FIGS. 13 and 14, as the first and second outer edges 110, 112 transition from the upper regions 148 to the lower regions 146, the first and second outer edges 110, 112 may extend outwardly away from at least the first and second inner boundaries 120, 122, respectively, so as to attain a second width along, or in the vicinity of, at least the lower edge 108, as indicated by w2 in FIG. 14. For example, as shown in FIGS. 13 and 14, the first and second outer edges 110, 112 along the lower regions 146, respectively, may extend away from at least the first and second inner boundaries 120, 122 such that at least a portion of the outer edge 110, 112 is generally aligned with the front edge 134a, 134b of the adjacent top or bottom segment 130, 132 of the foot gate 104. Thus, according to such embodiments, similar the front edges 134a, 134b of the top segment 130 and/or bottom segment 132, the lower region 146 of the first and second sidewall panels 114, 116 may also be configured to prevent or minimize exposure of the end of the user's foot to a variety of different types of trauma and/or pressure.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A therapeutic cushioning boot configured to receive a human leg, the therapeutic cushioning boot comprising:
   a rear panel configured to support a rear portion of the human leg, the rear panel including a first side, a second side, and a plurality of support chambers that are each uniformly filled with a fill material positioned within each of the plurality of support chambers, the plurality of support chambers including a first support chamber proximate the first side of the rear panel, a second support chamber proximate the second side of the rear panel, and a third support chamber provided on the rear panel between the first support chamber and the second support chamber;
   a first sidewall panel connected to the first side of the rear panel, the first sidewall panel configured to engage a first side portion of the human leg; and
   a second sidewall panel connected to the second side of the rear panel, the second sidewall panel configured to engage a second side portion of the human leg;
   wherein the fill material is the same fill material in each of the plurality of support chambers, and
   wherein the fill material in the first support chamber and the second support chamber is hyper-stuffed relative to the fill material in the third support chamber in greater concentration than the fill material in the third support chamber.

2. The therapeutic cushioning boot of claim 1 wherein the fill material is a polyester fiberfill material.

3. The therapeutic cushioning boot of claim 1 further comprising:
   a first boundary portion disposed between the first side of the rear panel and the first sidewall panel; and
   a second boundary portion disposed between the second side of the rear panel and the second sidewall panel.

4. The therapeutic cushioning boot of claim 3 wherein the first boundary portion is a first seam configured to facilitate folding of the first sidewall panel over the rear panel, and wherein the second boundary is a second seam configured to facilitate folding of the second sidewall panel over the rear panel.

5. The therapeutic cushioning boot of claim 3 wherein the first support chamber is an elongate chamber including a first support boundary defined along the first boundary portion and wherein the second support chamber is an elongate chamber including a first support boundary defined along the second boundary portion.

6. The therapeutic cushioning boot of claim 5 wherein the first support chamber further includes a second support boundary disposed on the rear portion and extending parallel to the first boundary portion, and wherein the second support chamber further includes a second support boundary disposed on the rear portion and extending parallel to the second boundary portion.

7. The therapeutic cushioning boot of claim 6 wherein the third support chamber is defined between the second support boundary of the first support chamber and the second support boundary of the second support chamber.

8. The therapeutic cushioning boot of claim 3 wherein the third support chamber extends from the first boundary portion to the second boundary portion.

9. The therapeutic cushioning boot of claim 1 further comprising a foot gate including a first segment coupled along a lower edge of the first sidewall panel and a second segment coupled along a lower edge of the second sidewall panel, wherein the first segment is releasably coupled to the second segment.

10. A therapeutic cushioning boot comprising:
    a foot portion configured to receive a foot of a user; and
    a leg portion connected to the foot portion and configured to receive a leg of the user, the leg portion including a plurality of support chambers arranged on a rear of the leg portion which support chambers are each uniformly filled with a fill material positioned within each of the plurality of support chambers, the plurality of support chambers including a first support chamber proximate a first side of the leg portion, a second support chamber proximate a second side of the leg panel, and a third support chamber provided between the first support chamber and the second support chamber, wherein the fill material is the same fill material in each of said first, second and third support chambers, and wherein the fill material in the first and second support chambers is hyper-stuffed relative to the fill material in the third support chamber and provided in greater concentration than the fill material in the third support chamber.

11. The therapeutic cushioning boot of claim 10 wherein the fill material is a polyester fiberfill material.

12. The therapeutic cushioning boot of claim 10 wherein the third support chamber is defined between the first support chamber and the second support chamber on the rear of the leg portion.

13. The therapeutic cushioning boot of claim 10 wherein the third support chamber extends from the first side to the second side of the leg portion and extends in front of the first support chamber and the second support chamber on the rear of the leg portion.

14. The therapeutic cushioning boot of claim 10 wherein the rear portion further includes a "V" shaped opening, wherein the first support chamber is positioned on a medial side of the "V" shaped opening, and wherein and second support chamber is positioned on a lateral side of the "V" shaped opening.

15. The therapeutic cushioning boot of claim 14 wherein the first support chamber and the second support chambers are elongate chambers that extend upward on the leg portion above the "V" shaped opening.

16. A therapeutic cushioning boot comprising:
    a foot portion configured to receive a foot of a user;
    a leg portion configured to receive a leg of the user, the leg portion including at least a first support chamber and a second support chamber provided on a rear panel of the leg portion;
    a first fiberfill material uniformly filling the first support chamber at a first concentration; and
    a second fiberfill material uniformly filling the second support chamber at a second concentration that is less than the first concentration,
    wherein the first fiberfill material is the same material as the second fiberfill material, and
    wherein the first fiberfill material is hyper-stuffed in the first support chamber relative to the second fiber fill material in the second support chamber.

17. The therapeutic cushioning boot of claim 16, further comprising a third support chamber uniformly filled with the same material as the first support chamber and at the first concentration, wherein the first support chamber and the third support chamber are elongated channels extending axially along the leg portion.

18. The therapeutic cushioning boot of claim 17 wherein the second support chamber extends between the first support chamber and the third support chamber.

* * * * *